(12) United States Patent
Popoff et al.

(10) Patent No.: US 7,204,976 B2
(45) Date of Patent: Apr. 17, 2007

(54) HIGH EFFICACY GEL WITH LOW GLYCOL CONTENT

(75) Inventors: Christine Popoff, Morganville, NJ (US); Suman Chopra, Dayton, NJ (US); Mardoqueo Bustos, Hillsboro, NJ (US); Xiaozhong Tang, Bridgewater, NJ (US); Lin Fei, Kendall Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 320 days.

(21) Appl. No.: 10/448,514

(22) Filed: May 30, 2003

(65) Prior Publication Data
US 2004/0241122 A1  Dec. 2, 2004

(51) Int. Cl.
| A61Q 15/00 | (2006.01) |
| A61K 8/00 | (2006.01) |
| A61K 8/04 | (2006.01) |
| A61K 8/06 | (2006.01) |

(52) U.S. Cl. .................. 424/65; 424/400; 424/401; 514/937; 514/938

(58) Field of Classification Search .......... 424/65, 424/400, 401; 514/937, 938
See application file for complete search history.

(56) References Cited

U.S. PATENT DOCUMENTS

| 4,058,597 A | 11/1977 | Passedouet et al. |
|---|---|---|
| 4,122,029 A | 10/1978 | Gee et al. |
| 4,673,570 A | 6/1987 | Soldati |
| 4,690,774 A | 9/1987 | Vishnupad et al. |
| 4,822,602 A | 4/1989 | Sabatelli |
| 4,900,542 A | 2/1990 | Parrotta, Jr. et al. |
| 4,937,069 A | 6/1990 | Shin |
| 4,944,938 A | 7/1990 | Potini |
| 4,948,578 A | 8/1990 | Burger et al. |
| 5,069,897 A | 12/1991 | Orr |
| 5,102,656 A | 4/1992 | Kasat |
| 5,162,378 A | 11/1992 | Guthauser |
| 5,232,689 A | 8/1993 | Katsoulis et al. |
| 5,290,570 A | 3/1994 | Nichols et al. |
| 5,393,518 A | 2/1995 | Kwass |
| 5,587,153 A | 12/1996 | Angelone, Jr. et al. |
| 5,599,533 A | 2/1997 | Stepniewski et al. |
| 5,833,965 A | 11/1998 | Sun et al. |
| 5,863,525 A | 1/1999 | Angelone, Jr. et al. |
| 5,891,424 A | 4/1999 | Bretzler et al. |
| 5,891,425 A | 4/1999 | Bretzler et al. |
| 5,902,570 A | 5/1999 | Bretzler et al. |
| 5,925,338 A | 7/1999 | Karassik et al. |
| 5,939,056 A | 8/1999 | Fletcher et al. |
| 5,972,319 A | 10/1999 | Linn et al. |
| 6,007,799 A | 12/1999 | Lee et al. |
| 6,010,688 A | 1/2000 | Shen |
| 6,042,816 A | 3/2000 | Shen |
| 6,051,216 A | 4/2000 | Barr et al. |
| 6,066,314 A | 5/2000 | Tang et al. |
| 6,183,730 B1 | 2/2001 | Guskey et al. |
| 6,267,970 B1 | 7/2001 | Matesevac et al. |
| 6,375,937 B1 | 4/2002 | Chopra et al. |
| 6,403,067 B1 | 6/2002 | Schamper et al. |
| 6,403,069 B1 | 6/2002 | Chopra et al. |
| 6,410,002 B2 | 6/2002 | Scafidi et al. |
| 6,419,910 B2 | 7/2002 | Ma et al. |
| 6,458,345 B1 | 10/2002 | Emslie et al. |
| 6,468,512 B1 | 10/2002 | Carmody |
| 6,485,716 B1 | 11/2002 | Fei et al. |
| 6,500,412 B1 | 12/2002 | Johansson et al. |
| 6,610,279 B2 | 8/2003 | Chopra et al. |
| 6,610,829 B2 | 8/2003 | Ni et al. |
| 6,983,845 B2 | 1/2006 | Shah et al. |
| 2002/0022010 A1 | 2/2002 | Emslie et al. |
| 2002/0192172 A1 | 12/2002 | Chopra et al. |
| 2003/0008787 A1 | 1/2003 | McGee et al. |
| 2003/0031638 A1 | 2/2003 | Joshi |
| 2004/0109833 A1 | 6/2004 | Tang et al. |
| 2004/0198998 A1 | 10/2004 | Holerca et al. |
| 2004/0241123 A1 | 12/2004 | Popoff et al. |
| 2004/0241196 A1 | 12/2004 | Popoff |
| 2004/0265255 A1 | 12/2004 | Holerca et al. |
| 2005/0019287 A1 | 1/2005 | Li et al. |

FOREIGN PATENT DOCUMENTS

| DE | 197 25 087 | 12/1998 |
|---|---|---|
| EP | 1 005 852 | 6/2000 |
| EP | 1 005 853 | 6/2000 |
| EP | 1777784 A | 2/2002 |
| JP | 03-033266 | 2/1991 |
| JP | 11130652 | 5/1999 |
| JP | 2001163752 | 6/2001 |
| WO | WO 91/18588 | 12/1991 |
| WO | WO 92/05767 | 4/1992 |
| WO | WO 97/23594 | 7/1997 |
| WO | WO 97/46246 | 12/1997 |
| WO | WO 01/39730 | 6/2001 |
| WO | WO 01/47479 | 7/2001 |
| WO | WO 01/62222 | 8/2001 |

*Primary Examiner*—Shelley A. Dodson
(74) *Attorney, Agent, or Firm*—Michael F. Morgan

(57) ABSTRACT

The invention is a clear, elastomer-free, gel composition comprising: (a) 14–30 weight % of an antiperspirant active having a low metal to chloride ratio; (b) 7–23.3 weight % of one or more cyclomethicones having a flash point of 100 degrees C. or less; (c) 0.6–0.9 weight % of a silicone surfactant having an HLB value$\leq 8$; (d) 30–70 weight % water; (e) 3.85–10 weight % of a water soluble glycol or polyglycol and (f) 0.1–3.0 weight % of a non-siliconized organic fragrance solubilizer; wherein the composition is a gel having a viscosity greater than 150,000 centipoise and a ratio of oil phase to water phase in the range of 10:90 to 24:76.

26 Claims, No Drawings

HIGH EFFICACY GEL WITH LOW GLYCOL CONTENT

FIELD OF THE INVENTION

The present invention is directed to a high efficacy gel composition which is a high viscosity water-in-oil emulsion (>150,000 cps at 21 degrees C.), is elastomer-free, and which comprises a glycine-complexed antiperspirant active (preferably with a lower metal to chloride ratio) along with a monovalent or divalent ionizable salt and a reduced amount of glycols in the active phase, as well as low levels of nonvolatile ingredients in the oil phase. The gel is formulated as clear products having reduced whitening and tack as well as reduced skin irritation.

BACKGROUND OF THE INVENTION

Antiperspirant products are well known in the art. Antiperspirants have appeared in the marketplace in varied dosage forms, such as sticks, soft solids, soft gels, roll-on, aerosols and creams. Generally, these dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes a continuous phase.

Of the above-referred-to dosage forms, the stick form is an example of a solid form, and the soft solid and soft gel are thickened forms which may or may not be solid (for example, under some circumstances, gels can flow). The stick form can be distinguished from a soft solid or soft gel in that, in a stick, the formulated product can retain its shape for extended time periods outside the package, the product not losing its shape significantly (allowing for some shrinkage due to solvent evaporation). Adjustment of amounts of gelling or thickening agents can be used in order to form a soft gel or stick.

Soft gels or soft solids can be suitably packaged in containers which have the appearance of a stick, but which dispense through apertures (for example, slots or pores) on the top surface of the package. The soft solid products have also been called soft sticks or "smooth-ons", and hereinafter are generically called "soft solids". Reference is made to U.S. Pat. No. 5,102,656 to Kasat, U.S. Pat. No. 5,069,897 to Orr, and U.S. Pat. No. 4,937,069 to Shin, each of which discloses such soft solids, including physical characteristics thereof such as viscosity and hardness. The contents of each of these three U.S. patents are incorporated herein by reference in their entirety for description of characteristics of soft solids and suitable packaging for such products.

Recently, there has been significant activity in developing clear antiperspirant sticks and soft gels, particularly to provide sticks and soft gels having increased efficacy (for example, by providing increased amounts of the antiperspirant active in the sticks and soft gels), improved cosmetic characteristics (including reduced whitening, reduced residue and reduced tack), and reduced skin irritation potential (e.g., providing a product that is "mild").

U.S. Pat. No. 4,944,938 to Potini discloses clear, non-alcoholic, quick drying, antiperspirant and deodorant gels, which are stable both at room temperatures and at higher temperatures, are non-stinging and leave no white residue on the skin. The gel is free of gelling agents, waxes, clays, or monohydric alcohols having 2–8 carbon atoms. The gels use 3–5 carbon atom trihydric alcohols as coupling agents which act as solubilizers in the system and keep the system stable and clear. The gels can include an aluminum active salt; a volatile water-insoluble emollient, such as isostearyl benzoate: a soluble emollient such as cetyl ether; solubilizers such as propylene glycol and glycerin; volatile siloxanes; and water.

Some cellulosic materials, such as hydroxypropylcellulose, among others, are compatible with polyvalent metal salts and have been used in the manufacture of clear lotions. These cellulosic materials, however, must be prepared with a high percentage of water or alcohol in order to insure solubilization of the active ingredient. The resulting formulations, in addition to a high irritation potential, are tacky and low in efficacy, when alcohol-based; and exhibit tackiness and along drying time when water-based.

Clear antiperspirant soft gels (which have been dispensed from containers having the appearance of stick) have recently been marketed, consisting of viscous, high-internal-phase emulsions. These soft gels exhibit some advantages over the aforementioned sticks, particularly acetal-based clear sticks, in that the selection of formulation ingredients is less restricted (for example, water can be used), and often tack can be reduced significantly. Concerning these emulsions, note U.S. Pat. No. 4,673,570 to Soldati and U.S. Pat. No. 4,900,542 to Parrotta, et al. These two U.S. patents disclose clear gelled antiperspirant compositions free of waxes and conventional gelling agents, containing a volatile silicone fluid, a silicone emulsifier, a destabilizing auxiliary emulsifier, water, non-volatile emollient, a coupling agent, an active antiperspirant component and ancillary agents such as perfume, coloring agents, etc. The silicone emulsifiers a cyclomethicone-dimethicone copolyol silicone fluid marketed by Dow Corning Corporation under the trademark DOW CORNING 3225C formulation. In particular, U.S. Pat. No. 4,673,570 claim 1 is "from about 10–25% by weight of a cyclomethicone-dimethicone copolysilicone fluid (same as 1.0–2.5% on an actives basis). The contents of these two U.S. patents are incorporated herein by reference in their entirety with respect to the features of the inventions described therein.

Also to be noted is PCT (International application) Publication No. WO 92/05767. This patent document discloses a clear gel-type cosmetic product having a viscosity of at least about 50,000 cps at 21 degrees C. and a refractive index of 1.3975–1.4025 at 21 degrees C., and having an optical clarity better than 50 NTU (Nephelometric Turbidity Units) at 21 degrees C., the product being an emulsion with a water phase having an active ingredient incorporated therein and with an oil phase. The refractive indices (measured at 5893 Angstroms) of the water and oil phases match to within 0.0004. The oil phase includes an emulsifier which when properly mixed with the water phase component yields a water-in-oil emulsion, and the water phase includes one or a combination of various polar species such as water, propylene glycol, sorbitol and ethanol. The water phase includes the deodorant and/or antiperspirant active ingredient. The contents of this PCT (International application) Publication No. 92/05767 are incorporated herein by reference in their entirety.

U.S. Pat. No. 6,007,799, assigned to the same owner as this case, describes clear cosmetic gels that are water-in-oil emulsions and which comprise at least one coupling agent, silicone fluids and an alkoxylated, alkyl substituted silicone surface active agent.

U.S. Pat. Nos. 5,587,153 and 5,863,525 issued to Gillette also describe gel products that (1) contain silicone in the oil phase and (2) does not control the propylene glycol content.

U.S. Pat. No. 5,925,338 issued to Gillette describes a clear gel comprising selected amounts of various types of silicones.

U.S. Pat. No. 6,419,910 assigned to Unilever describes a clear emulsion and gel-type antiperspirant and deodorant composition which comprises a water in oil emulsion which is essentially free of glycols and low and middle chain alcohols. The composition comprises 25–35% of an oil phase comprising at least one non-volatile ester or at least one nonvolatile silicone wherein at least one oil phase soluble ingredients has a refractive index of about 1.40 to about 1.45. The active phase contains a water soluble, non-simple glycol component which raises the refractive index of the aqueous solution.

U.S. Pat. No. 6,410,002 and U.S. Patent Application 2002/10051138 A1 also assigned to Unilever, describes an essentially glycol free clear emulsion and gel-type antiperspirant and deodorant composition in which the water phase further differentiated by containing at least one polymeric ethylene oxide glycol and is essentially free of glycols and low and middle chain alcohols U.S. Pat. No. 6,042,816 describes enhanced efficacy antiperspirant salt compositions containing calcium and an amino acid or a hydroxy acid, methods of making such enhanced efficacy antiperspirant salt compositions, stabilized aqueous solutions of such enhanced efficacy antiperspirant salt compositions, and topical compositions containing such enhanced efficacy antiperspirant salt compositions.

U.S. Pat. No. 6,468,512 assigned to Avon describes a clear antiperspirant/deodorant gel composition. The composition is a water-in-oil emulsion having a viscosity about 7,000 cps to about 25,000 cps and a clarity from about 30 NTU or less. The composition further has an antiperspirant active, water, silicone gelling agent, and one or more silicone oils.

U.S. Pat. No. 6,485,716 assigned to the same owner as the present case describes a clear, elastomer-free, gel composition comprising: (a) 0.1–25 weight % of an antiperspirant active having a low metal to chloride ratio in the range of 0.9–1.3:1; (b) 9–23.95 weight % of one or more volatile silicones having a flash point of 100 degrees C. or less; (c) 0.05–0.5 weight % of a silicone surfactant having an HLB value less than or equal to 8; (d) 30–70 weight % water; (e) 0–50 weight % selected water soluble organic solvents; and (f) 0–10 weight % of an emollient; wherein the composition is a liquid gel having a viscosity in the range of 5–50,000 centipoise and a ratio of oil phase to water phase in the range of 10:90 to 24:76.

U.S. Pat. No. 6,500,412 assigned to the same owner as this case describes a non-sticky, clear water-in-oil emulsion comprising: (a) 65–90 weight % of an internal phase comprising 5–35 weight % of an antiperspirant salt (anhydrous basis) having a metal:chloride ratio in the range of 0.9–1.4:1; 5–15 weight % of tripropylene glycol; and 35–70 weight % water; and (b) 10–35 weight % of an external phase comprising 1–40 weight % of a volatile silicone which is not an elastomer; 0.1–5 weight % of a silicone copolyol surfactant; and 0–20 weight % of a nonvolatile silicone which is not an elastomer; wherein the composition is free of (1) C1–5 saturated alcohols, (2) added propylene glycol, (3) elastomer gelling agents, (4) soap gelling agents (5) borate gelling agents, and (6) coupling agents, and wherein all amounts are in % by weight based on the total weight of the composition.

While various cosmetic gel compositions, including antiperspirant and deodorant compositions that are clear are known, it is still desired to provide a cosmetic gel composition (e.g., clear antiperspirant and/or deodorant gel composition) which has improved efficacy in comparison to other products, especially other commercially available gel products. It is a further object of the invention to provide products which have (a) reduced whitening, (b) low tack, (c) a quick dry down profile and (d) reduced skin irritation potential relative to commercially available products. It is yet another object of the invention to provide gel antiperspirant/deodorant products which are free of oil soluble high refractive index (>1.420) emollients (which tend to slow down drying time of the gel composition due to their low volatility). This invention has an oil phase which has a relatively low refractive index when compared to other clear gels, thereby reducing the level of water soluble organic or silicone based refractive index matching agents (such as glycols and other monohydric or polyhydric alcohols, ionizable monovalent or divalent inorganic salts, sugars, esters and amino acids) used to match the refractive index of the water (internal) phase to the oil (external) phase to obtain a clear gel.

SUMMARY OF THE INVENTION

The invention is a clear (50–250 NTU at 21.0 degrees C.), high efficacy gel composition which is a high viscosity (>150,000 centipoise) water-in-oil, elastomer-free emulsion. These gels comprise a glycine containing antiperspirant active with a low metal to chloride ratio in a high water content (>30 weight % of the formula) internal (aqueous) phase, a copolyol, and a fragrance solubilizer in the external phase. The external (oil) phase of the composition is free of silicone emollients that have a high refractive index (R.I.>1.4200). The gel compositions of this invention can include increased amounts of the cosmetically active ingredient (which must be added in an amount of at least 14 weight %). These cosmetic gels are quick drying due to the combination of low levels of nonvolatile materials in the oil phase and low levels (3.85–10 weight %) of glycols but provided that the amount of propylene glycol should not exceed 7.5 weight %. The overall level of silicone emollients is also controlled and is limited to $\leq 1$ weight %. Monovalent or divalent salt are used as refractive index modifying agents in the aqueous phase so as to match the refractive index of the oil phase, thus rendering a clear gel.

The invention is a clear water-in-oil emulsion having an external oil phase and internal water phase wherein:

(I) The Oil Phase Comprises:

(a) 7.0–23.3 weight % (more particularly 9–20 weight %) of one or more cyclomethicones having a flash point of 100 degrees C. or less;

(b) 0.6–0.9 weight % on an active basis (particularly 0.6–0.8% ) of a silicone surfactant having an HLB value (hydrophilic lipophilic balance)$\leq 8$);

(c) 0.1–3.0 weight % of an non-siliconized organic fragrance solubilizer (particularly 0.5–2%) consisting of silicone compatible straight or branched hydrocarbons with a molecular weight less than 1000, alkyl substituted phenyl esters with an alkyl carbon chain length between C-1 to C-20, and ethoxylated and or propoxylated ethers with a carbon chain length from C-1 to C-25 and ethoxylation and or propoxylation from 1–10 (for example, a member of the group consisting of hydrogenated polyisobutene (Polyiso 250), C12–15 alkyl benzoate (FINSOLV TN), and PPG-3 myristyl ether (particularly PPG-3 myristyl ether) which can help to solubilize the fragrance oils in the otherwise all silicone based oil phase and which does not negatively affect the skin feel and dry down characteristics of the composition. Aesthetic skin feel attributes such as wetness, stickiness, and residue have been evaluated by a 10 member trained panel both on the forearm and underarm by rating some of the antiperspirant gels described in this invention along with a commercial gel. Significant differences in performance between some of the formulas described herein and a commercial gel were noted at the 95% confidence level.

(d) 0–1 weight % (particularly 0–0.25 weight % or 0.1–1.0 weight %) of a low refractive index (R.I.<1.4200 at 21 degrees C.) silicone emollients (by definition excluding (a) and (b) of this section) selected from the group consisting of (i) volatile linear polydialkylsiloxanes with a flash point is $\leq 100$ degrees C. (particularly low viscosity dimethicones); (ii) nonvolatile linear polydialkylsiloxanes with a flash point >100 degrees C.; and (iii) silanols (for example dimethiconols such as DC 9023 and DC 1501 from Dow Corning) in which one or two of the alkyl groups of the foregoing materials (i) or (ii) are replaced with a hydroxyl group; (note that combinations of these low refractive index silicone emollients may also be used, however, the maximum level of silicone emollients must still be $\leq 1$ weight % (note that one particular embodiment of the invention is free of volatile linear silicones (e.g. volatile dimethicones) and/or free of non-volatile silicones).

(e) 0–5 weight % fragrance or odor masking component; and (II) The Aqueous Phase Comprises:

(a) 14–30 weight % on an anhydrous basis (particularly 17–30 weight % and, more particularly, 17–25 weight %) of a glycine containing antiperspirant active salt comprising either aluminum or aluminum and zirconium metals such that (i) if aluminum and zirconium salt is used then the metal/Cl ratio of the salt should be low, such as 0.9–1.3:1 (more particularly in the range of 0.9–1.05:1); the glycine/Zr ratio should be >1.2, and Peak-5/Peak-3 should be >1.0; (ii) if aluminum salt is used then the aluminum to chloride molar ratio should be in the range of 0.5–2.5:1; the glycine/Al molar ratio should be in the range of 0.05–0.26:1 (preferably in the range of 0.05–0.16:1);

wherein the glycine containing antiperspirant active salt has a pH in the range of 2–4 (when measured in water at a concentration of 15%), is free of any other halide scavenging material, and has a value of at least 0.50 for the ratio calculated as:

$$\frac{\text{area of Peak 5}}{\text{total area under Peak 2 + Peak 3 + Peak 4 + Peak 5}}$$

(b) 30–70 weight % water (particularly 45–65% and, more particularly, 50–60%);

(c) 3.85–10 weight % (particularly 4–8 weight %) of a water soluble glycol system which comprises at least 0.2% propylene glycol and an additional glycol component selected from the group consisting of ethylene glycol; diethylene glycol; triethylene glycol; tetraethylene glycol; propylene glycol; dipropylene glycol; tripropylene glycol; 1,3 propanediol; 2-methyl propanediol; methyl propanediol; 1,6-hexanediol; 1,3 butanediol; 1,4 butanediol; PEG-4 through PEG-600; PPG-9 through PPG-34; neopentyl glycol; trimethylpropanediol; 2,2 dimethyl-1,3propandiol; 2,2, 4,4-tetramethyl-1,3-cyclobutane-diol; and mixtures thereof in which the amount of propylene glycol does not exceed 7.5% (particularly not exceeding 5%). (More particular examples of the glycol component include one or more members of the group consisting of propylene glycol, dipropylene glycol, 2-methyl-1, 3 propanediol, methyl propylene glycol, low molecular weight (less than 600) polyethylene glycol and mixtures of any of the foregoing.)

(d) 0.2–4 weight % of a monovalent or divalent ionizable, water-soluble inorganic or organic salts to help increase the refractive index of the active phase and optimize the glycol level. These salts are of the form $M_aX_b$ where a=1, or 2 and b=1 or 2; M is a member selected from the group consisting of $Na^{+1}$, $Li^{+1}$, $K^{+1}$, $Mg^{+2}$, $Ca^{+2}$, $Sr^{+2}$ and $Zn^{+2}$ and X is a member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, hydrogensulfate. Salts of particular utility are NaCl and $ZnCl_2$.

(e) 0–5% of a water soluble carbon based high refractive index (R.I.>1.4200) agent selected from the group consisting of additional glycine (which is not part of the original salt), glycerin, trimethylglycine ("Betaine,"), alanine, diglycereth-7, triglycereth-7 citrate, glycereth-7 glycolate, glycereth-5 lactate, lauramidopropyl glycerin, glycereth-5 lactate, glycereth-7 glycolate, and glycereth-20 benzoate (Ethox GB-2) (for example, 0.5–3 weight % of a high refractive index agent selected from the group consisting of diglycereth-7 citrate, glycereth-7 glycolate, glycereth-5 lactate, lauramidopropyl glycerin, glycereth-5 lactate, glycereth-7 glycolate and glycereth-20 benzoate; or, as a second example, 0.5–3 weight % of a high refractive index agent selected from the group consisting of additional glycine (which is not part of the original salt), glycerin, trimethylglycine, and alanine;

(f) 0–10 weight % (particularly 0–4%) of an alcohol having 2–4 carbons (for example, 1–5% ethanol);

wherein (i) all amounts are based on the weight of the entire composition, (ii) the composition is an emulsion having a viscosity greater than 150,000 centipoise (for example, in the range of 150,000–600,000 centipoise, more specifically, 200,000–350,000 centipoise), and (iii) the composition has a ratio of oil phase to water phase in the range of 10:90 to 24:76, and (iv) the composition is free of elastomers, borate crosslinkers soap gelling agents, secondary water-soluble surfactants having an HLB value$\geq 9$.

Compositions of the invention according to a first aspect of the present invention, various of the foregoing objects are achieved through a high viscosity emulsion having (1) an aqueous phase containing water (or water and a water soluble organic solvent as defined above); the antiperspirant active containing aluminum and zirconium metals having a low M:Cl ratio (0.9 to 1.3:1; and at least one monovalent or divalent salt, a combination of propylene glycol and another glycol containing two hydroxy groups or polymeric glycol in which the total level of glycol species does not exceed 10 weight percent; and (2) an oil phase containing a volatile organic or silicone material, and the composition further including (3) a suitable silicone based surfactant such as an alkoxylated, alkyl substituted siloxane surface active agent in an amount of 0.6–0.9 weight % (on an actives basis) which suitable to form a high viscosity (>150,000 cps) gel as described above and (4) a suitable fragrance solublizer such as myristyl ether which helps to solubilize the fragrance oils in the predominantly silicone based oil phase.

The refractive index of the active phase is matched to the oil phase (comprised of fragrance, surfactants, fragrance solubilizers silicones) by adding glycols, monovalent and/or divalent salts and optionally monohydric alcohols such that the refractive index of the active phase differs from the refractive index of the oil phase by an amount of about 0.000 to 0.0040 units. This renders a clear product have an NTU (Nephelometric Turbidity Units) value in the range of between 50 and 250 and an R.I. in the range of 1.4025 to 1.4150. Most preferably the refractive index of the active phase is lower than that of the fragranced oil phase thereby minimizing the level of glycols. If added to the composition, the fragrance oils typically have refractive indices ranging from 1.4450–1.4850 and are used typically at levels ranging from 0.50–2.0 weight percent. Ionizable monovalent and divalent inorganic salts, antiperspirant salts, water and optional ingredients such as alcohol are optimized to provide a quick drying gel composition.

Refractive index measurements are made at a temperature of about 20–25 degrees C. using a Bausch and Lomb Abbe 3L Refractometer. Turbidity measurements as described herein are made with an Orbeco-Hellige #965 Direct-Reading Turbidimeter.

One embodiment of the invention is comprised of an oil phase composition such that the addition of the fragrance component (if fragrance is added to the composition) provides a refractive index in the range from about 1.4015 to about 1.4150; especially from about 1.4025 to about 1.4090.

One of the benefits of adding a non-siliconized organic fragrance solubilizer is to improve the solubility of the fragrance within the silicone (primarily cyclomethicones) based oil phase of the gel emulsion. The limited solubility of some fragrances in the cyclomethicone and linear polydialkylorganosiloxanes (if present) is easily determined by the turbidity of the aforementioned silicone(s) when approximately 10–30 weight % of fragrance is added to the silicone. To those skilled in the art, it is known that the addition of as little as 5–10 weight % (the amount depending on the fragrance) of the fragrance solubilizers previously described (e.g PPG-3 myristyl ether) to the silicone/fragrance mixture results in a clear solution.

The high viscosity gel compositions of the present invention include an antiperspirant active agent in an amount sufficient to have a deodorizing effect and/or in an amount sufficient to reduce the flow of perspiration when the composition is applied to a human. For the antiperspirant active used in the internal (also called "active") phase various antiperspirant active materials that can be utilized according to the present invention provided that they are soluble at a suitable concentration in the active phase.

Antiperspirant actives can be incorporated into compositions according to the present invention in amounts in the range of 14–30 weight % (on an anhydrous solids basis), particularly 17–25 weight % of the total weight of the composition. Mixtures of actives can also be used. The amount used will depend on the formulation of the composition. At amounts at the higher end of the range a good antiperspirant effect can be expected. As noted above, the active is preferably included in the compositions of the invention by premixing the active with water and possibly small amount of propylene glycol.

Antiperspirant actives can be incorporated into compositions according to the present invention in amounts as described above. At lower levels the antiperspirant active material may not completely reduce the flow of perspiration, but will reduce malodor, for example, by acting as an antimicrobial material. At amounts of 15–25% by weight of the total weight of the composition (on an actives basis), an antiperspirant effect may be observed.

Particularly preferred are antiperspirant actives having the specific low metal to chloride ratio specified above and those described in U.S. Pat. No. 6,375,937 and patent application assigned to the same owners as this case (U.S. Ser. No. 10/314,712 filed Dec. 9, 2002).

In one particular type of salt of interest, an aluminum zirconium tetrasalt with glycine is used wherein aluminum zirconium tetrachlorohydrex glycine salt having a metal to chloride ratio in the range of 0.9 to 1.2:1 (especially in the range of 0.9 to 1.1:1 and, more particularly in the range of 0.9 to 1.0:1); and a glycine:zirconium mole ratio greater than 1.2:1, particularly greater than 1.4:1. This type of salt may be made in a variety of ways as described in U.S. Pat. No. 6,375,937 as referenced above.

Another particular type of salt of interest is an aluminum chloride salt buffered by glycine, wherein the salt has a metal to chloride ratio in the range of 0.9 to 1.2:1 (especially in the range of 0.9 to 1.1:1 and, more particularly in the range of 0.9 to 1.0:1). Also of interest are salts which include Betaine, additional glycine, or another amino acid such as alanine to further increase the refractive index of the glycine-containing active complex.

Examples of salts include those made as follows:

Method A: An aluminum chlorohydrate (ACH) solution of ACH salt in water of suitable concentration is mixed with an aqueous solution of zirconyl chloride (ZrOCl$_2$) of suitable concentration and powdered glycine. The mixture is stirred at room temperature to obtain the salt.

Method B: A suitable commercially available aluminum zirconium tetrachlorohydrex glycine salt is obtained and mixed with a sufficient amount of an aqueous aluminum chloride (AlCl$_3$) solution and powdered glycine. The mixture is stirred at room temperature to obtain the salt. When Method B is used, a suitable salt to use as a starting material includes various types of tetra salts such as aluminum zirconium tetrachlorohydrex gly, aluminum zirconium tetrachlorohydrex gly propylene glycol complex, aluminum zirconium tetrachlorohydrex gly dipropylene glycol complex, and mixtures of any of the foregoing. These salts may be referred to hereinafter as experimental salts or carry an "exp" suffix in their designation. It is preferred that the experimental salt be used in the form of a 28–50% water solution when added to form the compositions of the invention.

The cyclomethicones used in this invention are one or more members selected from the group consisting of cyclic polydimethylsiloxanes such as those represented by Formula III:

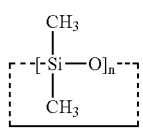

Formula III where n is an integer with a value of 4–6, particularly 5–6. These include a tetramer (D4), a pentamer (D5), and a hexamer (D6), and mixtures of any two or three of the forgoing. For example, DC-245 fluid and DC-345 from Dow Corning Corporation (Midland, Mich.) are types of cyclomethicones which can be used. It is to be noted that for purposes of the present invention cyclomethicones are not considered as silicone emollients.

Suitable silicone surfactants include silicone polyglucosides (for example, octyl dimethicone ethoxy glucoside) and silicone copolyols having an HLB value (hydrophilic lipophilic balance)≦8. The HLB value may be measured in a variety of ways such as described in conventional references or found listed in tables of data recording such values. It is intended that any type of HLB measurement technique may be used.

A silicone copolyol (especially dimethicone copolyol) may be used in an amount of 0.6–0.9 weight % (actives basis), particularly 0.6–0.8.

In general, silicone copolyols useful in the present invention include copolyols of the following Formulae I and II. Formula I materials may be represented by:

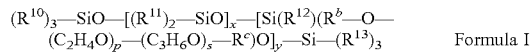

$(R^{10})_3$—SiO—$[(R^{11})_2$—SiO$]_x$—$[Si(R^{12})(R^b$—O—$(C_2H_4O)_p$—$(C_3H_6O)_s$—$R^c)O]_y$—Si—$(R^{13})_3$    Formula I wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an acyl group such as an ester with a terminating alkyl group of 1–4 carbons, or an aryl group such as phenyl; m has a value of two to eight; p and s have values such that the oxyalkylene segment —$(C_2H_4O)_p$—$(C_3H_6O)_s$— has a molecular weight in the range of 200 to 5,000; the segment preferably having fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. Most preferably p and s should each have a value of about 18 to 28.

A second siloxane polyether (copolyol) has the Formula II:

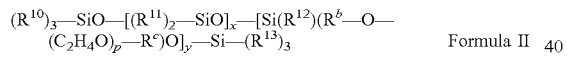

$(R^{10})_3$—SiO—$[(R^{11})_2$—SiO$]_x$—$[Si(R^{12})(R^b$—O—$(C_2H_4O)_p$—$R^c)O]_y$—Si—$(R^{13})_3$    Formula II wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^{13}$ substituents which are attached to the two terminal silicon atoms at the end of the siloxane chain can be substituted with the segment —$R^b$—O—$(C_2H_4O)_p$—$(C_3H_6O)_s$—$R^c$ or with the segment —$R^b$—O—$(C_2H_4O)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Particular examples of suitable dimethicone copolyols are available either commercially or experimentally from a variety of suppliers including Dow Coming Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING® 5225C from Dow Corning which is a 10% dimethicone copolyol in cyclomethicone; DOW CORNING® 2-5185C which is a 45–49% dimethicone copolyol in cyclomethicone; SILWET L-7622 from Witco; ABIL EM97 from Goldschmidt which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING® 2-5185 material is of particular interest.

In one particular embodiment 3–9 weight % (particularly 5–8%) of a 10% silicone copolyol such as dimethicone copolyol in cyclomethicone mixture may be used, wherein the amount of mixture added is selected so that the level of silicone copolyol in the cosmetic composition is in the range of 0.6–0.9% (particularly 0.6–0.8%) (for example, 6.5% of a 10% dimethicone copolyol in cyclomethicone mixture).

Emollient selection is limited to those which have a relatively low refractive index (R.I.<1.4200) in order to reduce the refractive index of the oil phase thereby making it easier to match the refractive index of the internal active phase. Emollients are a known class of materials in this art, imparting a soothing effect to the skin. They are ingredients which help to maintain the soft, smooth and pliable appearance of the skin. Emollients are also known to reduce whitening on the skin and/or improve aesthetics. Examples of suitable emollients which meet the low refractive index requirement are limited to silicone-based structures which are absent of phenyl groups.

Preferably linear silicones, are selected from the group consisting of polydialkylsiloxanes represented by the formulae:

(1) $(R^{10})_3SiO(Si(R^{11})_2O)_xSi(R^{12})_3$ where $R^{10}$, $R^{11}$ and $R^{12}$ can be the same or different and are each independently selected from the group consisting of C1–C10 alkyl (with particular examples being polydimethylsiloxanes (dimethicones), especially low viscosity dimethicones (viscosity <100 cps) (with the R groups and x values being selected to maintain the RI limits);

(2) silanols and/or dimethiconols in which one or two of the alkyl (such as methyl) groups of the foregoing formula may be replaced with a hydroxyl group and is represented by formulae:

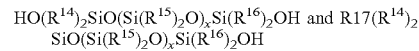

$HO(R^{14})_2SiO(Si(R^{15})_2O)_xSi(R^{16})_2OH$ and $R17(R^{14})_2SiO(Si(R^{15})_2O)_xSi(R^{16})_2OH$ where $R^{14}$, $R^{15}$ and $R^{16}$ and $R^{17}$ can be the same or different and are each independently selected from the group consisting of C1–C10 alkyl (with a particular example being methyl) (with the R groups and x values being selected to maintain the RI limits);

Particular examples of suitable silicone emollients include, but are not limited to, members of the group consisting of dimethicones having a viscosity in the range of 0.5–5.0 centistokes (e.g. Dow Corning® DC 200), dimethiconol (Dow Corning® DC1501), Dow Corning 2501 cosmetic wax (dimethicone copolyol) dimethiconol behenate, $C_{30-45}$ alkyl methicone, stearoxytrimethylsilane, and stearyl dimethicone) as well as silanol DC 9023 also from Dow Corning).

The low refractive index emollient or emollient mixture or blend thereof incorporated in compositions according to the present invention can, illustratively, be included in amounts of 0–1 weight % inclusive, preferably 0.5–1%.

The oil phase according to the present invention is, desirably, a silicone oil phase, so as to provide a water-in-silicone oil emulsion. The total of oil phase and siloxane surface-active agent preferably makes up from about 10% to about 24% by weight, of the total weight of the composition. This surface-active agent is an emulsifier which, when properly mixed with the aqueous phase components, and oil phase components, yields a water-in-oil emulsion. The oil phase is desirably a blend of liquids, but does not contain any significant amount of non-volatiles (that is, less than 1.0 weight % of any material having a flash point greater than 100 degrees C.). Moreover, the nonvolatile silicone based emollients described in this composition all have a refractive index lower than 1.420.

The refractive index of the oil phase (including fragrance) is determined, and, if necessary, adjusted to be in the range of 1.4015 to about 1.4150; especially from about 1.4025 to about 1.4090 and the refractive index of the aqueous phase is determined and adjusted (if necessary) to differ from the refractive index of the oil phase by less than 0.0050, preferable less than 0.0030 units. The aqueous phase is then mixed with the oil phase (for example, the aqueous phase is slowly added to the oil phase with turbulent agitation), and then additional additives, or other active ingredients, are added with mixing. Alternatively the fragrance can be added after the active phase is added to the oil phase. In this instance the refractive index of the oil phase (absent of fragrance) and aqueous phase should differ less than 0.0020. The resulting emulsion is then passed through, for example, a colloid mill or other high shear emulsifier so as to provide a viscous gel, the gel then being transferred to a suitable applicator or container for use by the consumer. Desirably, according to the present invention the aqueous phase further includes a glycol mixture consisting of propylene glycol and 2-methyl propanediol and/or dipropylene glycol providing advantages in the final product as discussed previously.

A particular example of an alkoxylated, alkyl substituted siloxane surface active agent is preferably, but not limited to, a dimethicone copolyol. An illustrative alkoxylated silicone-containing surfactant utilizable according to the present invention is cetyl dimethicone copolyol, referred to in U.S. Pat. No. 5,162,378 to Guthauser. Illustratively, the alkoxylated, alkyl substituted siloxane surface active agent is included in the composition in an amount of 6.0% to 9.0% by weight, of the total weight of the composition. Another example of a suitable surfactant is octyl dimethicone ethoxy glucoside (from Wacker-Belsil, Adrian, Mich.).

A specific cyclomethicone-dimethicone copolyol fluid which can be utilized to provide the alkoxylated silicone-containing surface-active agent is a mixture of cyclomethicone and dimethicone copolyol designated as DC 5225C from Dow Corning Corporation. This is a polyether substituted silicone of cyclomethicone and dimethicone copolyol (refractive index (RI)=1.3994) at about 20–25 degrees C. This DC 5225C, which is an emulsifying agent, is useful for preparing stable water-in-oil emulsions where a silicone makes up a large portion of the oil phase, and is a dispersion of a silicone surfactant (dimethicone copolyol) (10% by wt.) in cyclomethicone (Dow Corning 245) (90% by weight).

The mixture of cyclomethicone and dimethicone copolyol fluid is present in the composition, illustratively, in an amount of from about 7.0% to about 23.3% by weight, of the total weight of the composition.

According to another aspect of the present invention, the aqueous phase of the clear cosmetic gel composition further includes a glycol system in low amount (3.85–10 weight % preferably 4–8%) comprising propylene glycol and, preferably, at least one other glycol or polyglycol to help increase the refractive index of the active phase so as to match it within 0.0000–0.0040 units (preferably 0.0010–0.0030 units) of the fragranced oil phase. Illustratively, tripropylene glycol can be utilized as the additional polypropylene glycol. According to this aspect of the present invention, propylene glycol can be used in combination with the glycols up to a limited amount. Incorporation of glycols, particularly MP-diol (2-methyl 1,3 propanediol) and dipropylene glycol in the gel composition also improves cosmetic properties, including a reduction of tack and a decrease in the whitening and in the residue after application of the composition. Moreover, compositions incorporating polypropylene glycol, particularly, tripropylene glycol, have improved mildness (that is, reduced skin irritation potential) relative to commercially available products. The glycol or polyglycol is selected from the group consisting of ethylene glycol, propylene glycol, 1,2 propanediol, 2-methyl propanediol, diethylene glycol, triethylene glycol, tetraethylene glycol, dipropylene glycol, tripropylene glycol, methyl propanediol, 1,6-hexanediol, 1,3 butanediol, 1,4 butanediol, PEG-4 through PEG-600, PPG-9 through PPG-34, neopentyl glycol, trimethylpropanediol, 2,2 dimethyl-1,3 propanediol, 2,2,4,4-tetramethyl-1,3-cyclobutane-diol and mixtures thereof. More particular examples of the glycols which can be used with the propylene glycol are one or more members of the group consisting of dipropylene glycol, 2-methyl-1, 3 propanediol, methyl propylene glycol, low molecular weight (less than 600) polyethylene glycol and mixtures of any of the foregoing in which the amount of propylene glycol does not exceed 7.5%.

Clear gel compositions of the invention further include at least one ionizable inorganic salt which helps to increase the refractive index of the active phase and optimize the glycol level. Higher levels of glycols, although good for reducing tackiness tend to increase dry-down time. These ionizable salts are of the form $M_aX_b$ where a=1, or 2 and b=1 or 2; M is a member selected from the group consisting of $Na^{+1}$, $Li^{+1}$, $K^{+1}$, $Mg^{+2}$, $Ca^{+2}$, $Sr^{+2}$ and $Zn^{+2}$ and X is a member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, hydrogensulfate. Salts of particular utility are NaCl and $ZnCl_2$. As will be appreciated by those skilled in the art, while it may be possible under certain circumstances to add a salt directly to a portion of the mixture during manufacturing, it is preferred to add the salt as a mixture or solution of the salt in a carrier or solvent, particularly water. Of course various concentrations of the salt premix can be made such as in the range of 1–40%.

The present invention also includes methods of forming high viscosity cosmetic gel compositions described herein. In such methods an aqueous phase comprising water and the antiperspirant active is formed separately from the oil phase containing an alkoxylated, alkyl substituted siloxane surface active agent, an organic fragrance solubilizer and cyclomethicone and optional fragrance. The two phases are then combined and homogenized to achieve the desired viscosity.

For one embodiment the active phase is a water phase containing 17–30 weight % (anhydrous) of the low metal: chloride glycine-containing antiperspirant active, 4.05–14 weight % of the water-soluble glycol system with the monovalent or divalent ionizable water-soluble salt. Illustratively, free water is included in the composition in the range of 30–70 weight % based on the total weight of the composition. The water phase can also include, for example, (along with the antiperspirant active, water-soluble glycol system and ionizable divalent or monovalent salt) 1–5 weight % of a water-soluble carbon-based, high refractive index agent (particularly additional glycine (an additional amount that is not part of the original salt), glycerin, alanine and/or Betaine (as defined above, trimethylglycine).

These compositions of the present invention may be prepared by a batch process, or a continuous or semi-continuous process, and the processes yield compositions which are stable, highly efficacious and possess excellent aesthetic qualities.

The compositions according to the present invention are used as conventional cosmetic gel compositions. For example, where the composition according to the present invention is a clear antiperspirant soft gel composition, packaged in a dispensing container having a top surface with slots or pores, the gel is extruded from the dispensing container through the slots or pores and applied to the skin (for example, in axillary regions of the human body) by rubbing the soft gel material extruded through the top surface of the container on the skin in the axillary region.

As a further aspect of the present invention, the dispensing container can be clear and can be tinted so as to for example, fit to the fragrance hedonics. The composition has reduced tack, quick dry down, a cool sensation, and a silky feel and imparts much less or no white residue on dry down compared to commercially available products. Moreover, compositions of the present invention incorporating a polypropylene glycol component have improved mildness (have reduced skin irritation potential) as compared to commercially available products, and have improved cosmetic properties (including reduced tackiness) and reduced white residue upon application. The gel emulsions according to the present invention are stable and optically clear are cosmetically elegant, and are capable of being delivered from a suitable applicator package.

Throughout the present specification, the antiperspirant active materials, when utilized in an antiperspirant effective amount in the composition, act to reduce body malodor by reducing production of perspiration; however, these antiperspirant active materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor absorbents, as antimicrobial agents, as agents chemically reacted with malodorous materials, etc.

The amount of active component that can be used will vary with the particular active ingredient incorporate. The product comprises antiperspirant active materials in amounts sufficient to combat body malodor either as a deodorant or as an antiperspirant when applied to the axillary regions of the body. As a general rule, an antiperspirant product should contain an active antiperspirant material in an amount anywhere from about 9% to about 25% by weight, of the total weight of the composition. However, for the present invention it has been found that a minimum of at least 14 weight % of antiperspirant salt must be used to obtain the clarity desired. The active antiperspirant material utilized in the compositions of the present invention can be pre-dissolved in water or in another solvent (for example, in propylene glycol), and may be buffered or unbuffered. Preferably, the antiperspirant materials are present in solution in a solvent.

Where a deodorant active material is utilized other than lower amounts of an antiperspirant active, any deodorant active material, which can be dissolved in the oil phase, can be utilized in an amount sufficient to have a deodorant effect. Illustratively, the deodorant active material can be 2,4,4'-trichloro-2'-hydroxy diphenyl ether (triclosan), and/or benzethonium chloride and/or octoxyglycerin (Sensiva® SC 50). Where the deodorant ingredient is used in place of the antiperspirant active ingredient, a deodorant gel composition (rather than an antiperspirant gel composition) would be provided.

Throughout the present specification, where compositions are described as including or comprising specific components or materials, it is contemplated by the inventors that the compositions of the present invention also consist essentially of, or consist of, the recited components or materials. Accordingly, throughout the present disclosure any described composition of the present invention can consist essentially of, or consist of, the recited components or materials.

A desired feature of the present invention is that a clear cosmetic gel composition (e.g., clear deodorant or antiperspirant gel composition) can be provided. The term clear (that is clarity), according to the present invention, is intended to connote its usual dictionary definition; thus, a clear, e.g., cosmetic gel composition of the present invention allows ready viewing of objects behind it. By contrast, a translucent composition allows light to pass through, but causes the light to be so scattered that it will be impossible to see objects behind the translucent composition. Optical clarity of compositions of the present invention can be measured using a turbidmeter as described above, and desirably lies between 50 and 250 NTU measured at room temperature (20°–25° C.).

Moreover, the clear cosmetic gel composition of the present invention, which is in the form of a macro-emulsion as contrasted to a micro-emulsion, does not need to contain wax or gelling agents such as soaps, cellulosic materials or alginates. Furthermore, the composition according to the present invention does not require polydimethylcyclosiloxane, although the present compositions may contain this material. comprising 3–7 weight % of propylene glycol in combination with either 2-methyl propane diol or dipropylene glycol.

Several particular embodiments include those comprising one or more of the following: 1–4 weight % of ethanol or propanol; 9–20 weight % of the one or more cyclomethicones; 0.6–0.8 weight % of the silicone surfactant; 0.5–2 weight % of the fragrance solubilizer; and 45–65 weight % water.

Various materials incorporated in the water-based phase and in the oil-based phase, and their refractive indices (as measured using the Bausch and Lomb Abbe 3L Refractometer) are set forth in the following particular formulations:

6.0–9.0 weight % dimethicone copolyol/cyclomethicone (10%) (for example, Dow Corning 5225C);

7–23.3 weight % preferably 8–15 weight percent cyclomethicone (D4, D5, D6 or mixtures thereof);

0.1–3.0 weight % PPG-3 myristyl ether;

17–25 weight % antiperspirant active (for example, Al—Zr tetrachlorohydrex gly (such as Z-522, 27.5% from Summit Research Labs, Huguenot, N.Y.) and aluminum dichlorohydrate (such as Westchlor 100, 36.1% to which glycine has been added so that the molar ratio of gly/Al is in the range of 0.05–0.26:1) such as, for example, described in U.S. Pat. No. 6,375,937 and patent application assigned to the same owners as this case U.S. Ser. No. 10/314,712 filed Dec. 9, 2002);

30–70 weight % water;

0.2 to 4.0 weight % of an ionizable salt or combinations of ionizable salts of the form $M_aX_b$ where a=1 or 2; b=1 or 2; M is a member selected form the group consisting of $Na^{+1}$, $Li^{+1}$, $K^{+1}$, $Mg^{+2}$, $Sr^{+2}$ and $Zn^{+2}$, $Ca^{+2}$ and X is a member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, malonate, maleate, succinate, carbonate, bicarbonate, sulfate and hydrogensulfate (preferred salts are $ZnCl_2$ and NaCl or combinations thereof);

4–8 weight % of the glycol system as described above in the definition of the invention;

0–1 weight % of a low refractive index emollients (RI<1.4200) such as dimethiconol, dimethicones, silanol and combinations thereof;

0–1.0 weight % sage oil (any type such as Clary or Dalmation);

0–5 weight % fragrance or odor masking component;

0–10% of a water soluble non-glycol organic solvent selected from the group consisting of 2–4 carbon chain alcohols (for example ethanol), 0–5 weight % of a water-soluble carbon based high refractive index agent such as additional glycine which is not part of the original salt, trimethylglycine, alanine, glycerin, Diglycereth-7, Triglycereth-7 citrate, glycereth-7 glycolate, glycereth-5 lactate, lauramidopropyl glycerin, glycereth-5 lactate, Glycereth-7 glycolate, and glycereth-20 benzoate;

wherein the composition has a phase ratio in the range of 10:90–25:75 of oil to water and a viscosity is in the range of 150,000–600-000 centipoise.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997). Refractive Indices ("RI") are determined at a temperature in the range of 20–25 degrees C.

Examples 1–25

For Examples shown in Tables A through C the following procedure may be used with the types and amounts of ingredients. The sample sizes are about 500 grams. Silicone copolyol, cyclomethicone and fragrance are weighed and combined in a beaker. The mixture is stirred at 400–600 rpm using a Lightnin Mixer Model LI003. After the mixture becomes visually homogeneous, the active phase containing the antiperspirant active and ionizable salts in water and the rest of the ingredients (propylene glycol and MP diol) are added to the oil phase while mixing. The entire mixture is mixed for 15 minutes. The mixture is then homogenized for 2–4 minutes at a reading of 50–70 on Powerstat Variable Transformer (Superior Electric Co., Bristol, Conn.) using a homogenizer from Greerco Corp. (Hudson, N.H.).

TABLE A

| Ingredients (weight %) | Ex. 1 | Ex. 2 | Ex. 3 | Ex. 4 | Ex. 5 |
|---|---|---|---|---|---|
| Cyclomethicone | 12.00 | 12.00 | 10.70 | 11.50 | 10.50 |
| Dimethicone copolyol/cyclomethicone (DOW Corning 5225C, (10%) | 6.00 | 6.00 | 6.50 | 6.50 | 6.50 |
| Myristyl ether | 2.00 | 2.00 | 1.80 | 1.00 | 2.00 |
| Fragrance | 1.00 | 1.00 | 1.0 | 1.0 | 1.0 |
| Active A* | 69.70 | 69.70 | 70.00 | 70.0 | 0.00 |
| Active A** | 0.00 | 0.00 | 0.00 | 0.00 | 64.6 |
| MP Diol | 3.50 | 3.50 | 0.30 | 0.00 | 0.00 |
| Dipropylene glycol | 0.00 | 0.00 | 0.00 | 3.55 | 4.70 |
| Water | 3.30 | 2.46 | 2.70 | 3.40 | 7.80 |
| Zinc chloride solution (70.5 w/w %) | | 2.84 | 2.60 | 2.75 | 2.60 |
| NaCl (granular) | 2.00 | 0.00 | 0.00 | 0.00 | 0.00 |
| Propylene glycol | 0.50 | 0.50 | 4.40 | 0.30 | 0.30 |

*Al—Zr tetrachlorohydrex glycine complex (Z522, 27.5% in water from Summit Research Labs) which is a salt of the type described in Methods A and B above.

**Al—Zr tetrachlorohydrex glycine complex (Z522, 29.3% in water from Summit Research Labs).

TABLE B

| | (with ethanol) | | | | | | | | |
|---|---|---|---|---|---|---|---|---|---|
| Ingredient (weight %) | Ex. 6 | Ex. 7 | Ex. 8 | Ex. 9 | Ex. 10 | Ex. 11 | Ex. 12 | Ex. 13 | Ex. 14 |
| Cyclomethicone | 11.00 | 10.50 | 10.50 | 10.50 | 8.50 | 10.50 | 9.5 | 10.5 | 10.70 |
| Dimethicone copolyol/Cyclomethicone (Dow Corning 5225C, 10%) | 6.00 | 6.50 | 6.50 | 6.50 | 8.50 | 6.50 | 6.50 | 6.50 | 6.5 |
| PPG-3 myristyl ether | 2.00 | 2.00 | 2.00 | 2.00 | 2.00 | 2.00 | 3.00 | 2.00 | 1.80 |
| Fragrance | 1.00 | 1.00 | 1.00 | 1.00 | 1.00 | 1.00 | 1.0 | 1.0 | 1.00 |
| Active A* | 70.00 | 0.00 | 0.00 | 0.00 | 68.50 | 0.00 | 69.00 | 70.00 | 0.00 |
| Active A** | 0.00 | 64.40 | 64.40 | 64.57 | 0.00 | 0.00 | 0.00 | 0.00 | |
| Summit Z498*** | 0.00 | 0.00 | 0.00 | 0.00 | 0.00 | 66.5 | | | |
| Westchlor 100**** | 0.00 | 0.00 | 0.00 | 0.00 | 0.00 | 0.00 | 0.00 | 0.00 | 55.00 |

TABLE B-continued (with ethanol)

| Ingredient (weight %) | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|
| Water | 0.25 | 6.00 | 5.40 | 5.80 | 0.8 | 1.10 | 0.00 | 0.40 | 12.30 |
| glycine | 0.00 | 0.00 | 0.00 | 0.00 | 0.00 | 0.00 | 0.00 | 0.00 | 1.30 |
| MP Diol | 4.00 | 4.2 | 6.00 | 0.00 | 0.00 | 0.00 | 0.00 | 0.00 | 5.00 |
| DPG | 0.00 | 0.00 | 0.00 | 4.20 | 5.30 | 7.0 | 6.00 | 4.20 | 0.00 |
| Zinc Chloride (70.5 w/w % aqueous. solution) | 0.00 | 2.60 | 1.40 | 2.60 | 2.60 | 2.60 | 2.60 | 2.60 | 2.60 |
| NaCl | 2.50 | 0.00 | 0.00 | 0.00 | 0.00 | 0.00 | 0.00 | 0.00 | 0.00 |
| ethanol | 3.00 | 2.50 | 2.50 | 2.50 | 2.50 | 2.50 | 2.10 | 2.50 | 3.50 |
| Propylene glycol | 0.25 | 0.30 | 0.30 | 0.30 | 0.30 | 0.30 | 0.30 | 0.30 | 0.30 |

*Al—Zr tetrachlorohydrex glycine complex (Z522, 28% in water; M:Cl ratio of 1.0:1.0 from Summit Research Labs).
**Al—Zr tetrachlorohydrex glycine complex (Z522, 29% in water; M:Cl ratio of 1.0:1.0 from Summit Research Labs).
***Al—Zr tetrachlorohydrex glycine complex (29% in water; M:Cl ratio of 1.2:1.0 from Summit Research Labs).
****Aluminum dichlorohydrate complex (36% in water from Westwood Chemicals, Middletown, N.Y.)

TABLE C

| Ingredient (weight %) | Ex. 15@ | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|---|
| Cyclomethicone | 10.0 | 11.00 | 11.00 | 8.20 | 9.7 | 11.00 | 9.00 | 11.00 | 10.50 | 9.70 | 9.70 |
| Dimethicone copolyol/cyclomethicone (Dow Corning 5225C, 10%) | 6.00 | 6.00 | 6.00 | 8.00 | 6.50 | 6.00 | 6.00 | 6.00 | 6.00 | 6.50 | 6.50 |
| Dimethicone 200 50 cst | 0.0 | 0.0 | 0.0 | 0.0 | 0.0 | 0.0 | 0.0 | 0.00 | 0.00 | 1.00 | 1.00 |
| Dimethiconol (DC 1501) | 2.00 | 1.00 | 1.00 | 1.00 | 1.00 | 1.00 | 1.00 | 1.00 | 0.00 | 0.00 | 0.00 |
| PPG-3 myristyl ether | 2.00 | 2.00 | 2.00 | 1.80 | 1.80 | 2.00 | 2.00 | 2.00 | 2.5 | 1.80 | 1.80 |
| Fragrance | 1.00 | 1.00 | 1.00 | 1.0 | 1.00 | 1.00 | 1.00 | 1.00 | 1.0 | 1.0 | 1.0 |
| Active A** | 69.70 | 70.00 | 70.00 | 69.50 | 70.00 | 70.00 | 71.00 | 70.00 | 68.0 | 70.0 | 70.0 |
| MP Diol | 3.50 | 1.7 | 2.20 | 4.20 | 4.00 | 3.70 | 4.80 | 0.00 | 5.00 | 4.00 | 3.50 |
| Ethox 6B-2*** | 0.00 | 0.00 | 0.00 | 0.00 | 0.00 | 0.00 | 0.00 | 1.0 | 0.00 | 0.00 | 0.00 |
| Glycereth-7-malate | 0.00 | 0.00 | 0.00 | 0.00 | 0.00 | 0.00 | 0.00 | 0.00 | 1.4 | 0.00 | 0.00 |
| Water | 3.30 | 2.05 | 1.35 | 3.45 | 3.10 | 3.00 | 2.90 | 2.75 | 1.90 | 3.10 | 1.10 |
| Zinc chloride sol. (70.5 w/w % aqueous solution) | 0.0 | 0.0 | 2.70 | 2.60 | 2.60 | 0.00 | 0.00 | 0.00 | 2.20 | 2.60 | 2.60 |
| NaCl (granular) | 2.00 | 2.5 | 0.00 | 0.00 | 0.00 | 2.00 | 2.00 | 2.50 | 0.00 | 0.00 | 0.00 |
| ethanol | 0.00 | 2.50 | 2.50 | 0.00 | 0.0 | 0.0 | 0.00 | 2.50 | 0.00 | 0.00 | 2.50 |
| Propylene glycol | 0.50 | 0.25 | 0.25 | 0.25 | 0.30 | 0.30 | 0.30 | 0.25 | 1.5 | 0.30 | 0.30 |
| Total | 100 | 100 | 100 | 100 | 100 | 100 | 100 | 100 | 100 | 100 | 100 |

**Al—Zr tetrachlorohydrex glycine complex (Z522, 27.5% in water from Summit Research Labs) which is a salt of the type described in Methods A and B above.
***Glycereth-20-benzoate
@Ex. 15 is a comparative example which had inferior aesthetics.

The invention claimed is:

1. A composition comprising a water-in-oil emulsion having an external oil phase and internal water phase wherein:
   (I) the oil phase comprises:
      (a) 7.0–23.3 weight % of one or more cyclomethicones having a flash point of 100 degrees C. or less;
      (b) 0.6–0.9 weight % of a silicone surfactant having a hydrophilic lipophilic balance ≦8; and
      (c) 0.1–3.0 weight % of a non-siliconized organic fragrance solubilizer; and
   (II) the aqueous phase comprises:
      (a) 14–30 weight % on an anhydrous basis of a glycine containing antiperspirant active salt comprising either aluminum or aluminum and zirconium metals provided that
         (i) if an aluminum and zirconium salt is used then the metal/Cl ratio of the salt is in the range of 0.9–1.3:1, the glycine/Zr ratio is >1.2, and Peak-5/Peak-3 is >1.0; and
         (ii) if an aluminum salt is used then the aluminum to chloride molar ratio is in the range of 0.5–2.5:1, and the glycine/Al molar ratio is in the range of 0.05–0.26:1;

wherein the glycine containing antiperspirant active salt has a pH in the range of 2–4 when measured in water at a concentration of 15%, is free of any other halide scavenging material, and has a value of at least 0.50 for a ratio calculated as:

$$\frac{\text{area of Peak 5}}{\text{total area under Peak 2 + Peak 3 + Peak 4 + Peak 5}};$$

(b) 30–70 weight % water;
(c) 0.3–10 weight % of a water soluble glycol system which comprises at least 0.2% propylene glycol and an additional glycol component, in which the amount of propylene glycol does not exceed 7.5%; and
(d) 0.2–4 weight % of a monovalent or divalent ionizable, water soluble inorganic or organic salt of formula $M_aX_b$ where a=1, or 2 and b=1 or 2; M is a member selected from the group consisting of $Na^{+1}$, $Li^{+1}$, $K^{+1}$, $Mg^{+2}$, $Ca^{+2}$, $Sr^{+2}$ and $Zn^{+2}$ and X is a member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, hydrogensulfate;
wherein the composition is a clear emulsion;
wherein the composition has a ratio of oil phase to water phase in the range of 10:90 to 24:76;
wherein the composition has a viscosity fo greater than 150,000; and
wherein the composition is free of elastomers, borate crosslinkers soap gelling agents, and seccondary water-soluble surfactants having an HLB value ≧9.

2. The composition of claim 1 having a viscosity greater than 150,000 to 600,000.

3. The composition of claim 2 having a viscosity in the range of 200,000–350,000 cps.

4. The composition of claim 1 wherein the clarity of said product is between 50 and 250 NTU at 21 degrees C.

5. The composition of claim 1 wherein the refractive index of said product is between 1.4025 and 1.4150.

6. The composition of claim 1 wherein the aluminum to chloride molar ratio of the antiperspirant salt is in the range of 0.05–0.26:1.

7. The composition of claim 1 wherein the aluminum to chloride molar ratio of the antiperspirant salt is in the range of 0.05–0.16:1.

8. The composition of claim 1 comprising 17–25 weight % of the antiperspirant active.

9. The composition of claim 1 wherein the ionizable salt is selected from the group consisting of NaCl and $ZnCl_2$.

10. The composition of claim 1 wherein the water soluble glycol system is a member selected from the group consisting of propylene glycol; dipropylene glycol; tripropylene glycol; 2-methyl-1,3 propanediol; 1,3 propanediol; methyl propylene glycol; low molecular weight polyethylene glycol; and mixtures of any of the foregoing in which the amount of propylene glycol does not exceed 5%.

11. The composition of claim 1 wherein the water phase includes 1–5 weight % of ethanol.

12. The composition of claim 1 additionally comprising 0.5–3 weight % of a water soluble carbon based high refractive index agent selected from the group consisting of triglycereth-7 citrate, glycereth-7 glycolate, and glycereth-5 lactate.

13. The composition of claim 1 additionally comprising 0.5–3 weight % of a water soluble carbon based high refractive index agent selected from the group consisting of additional glycine, glycerin, trimethylglycine and alanine.

14. The composition of claim 1 wherein the silicone surfactant is a silicone copolyol selected from the group consisting of compounds of Formulae I and II wherein:
(a) Formula I is:

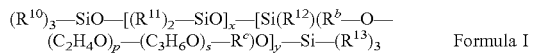  Formula I wherein each of $R^{10}$, $R^{11}$, $R^{12}$ and $R^{13}$ may be the same or different and each is selected from the group consisting of C1–C6 alkyl; $R^b$ is the radical $—C_mH_{2m}—$; $R^c$ is a terminating radical which is hydrogen, an alkyl group of one to six carbon atoms, an acyl group which is an ester with a terminating alkyl group of 1–4 carbons, or a phenyl group; m has a value of two to eight; p and s have values such that oxyalkylene segment $—(C_2H_4O)_p—(C_3H_6O)_s—$ has a molecular weight in the range of 200 to 5,000; the oxyalkylene segment has fifty to one hundred mole percent of oxyethylene units $—(C_2H_4O)_p—$ and one to fifty mole percent of oxypropylene units $—(C_3H_6O)_s—$; x has a value of 8 to 400; and y has a value of 2 to 40;
(b) Formula II is:

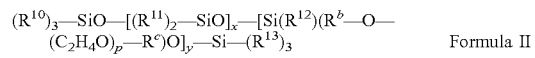  Formula II wherein p has a value of 6 to 16; x has a value of 6 to 100; and y has a value of 1 to 20 and other moieties have the same definition as defined in Formula I; and
(c) alternate embodiments of both Formulae I and II wherein the linking group $R^b$, the oxyalkylene segments, and the terminating radical $R^c$ occupy positions bonded to the ends of the siloxane chain and are not bonded to a silicon atom in the siloxane chain.

15. The composition of claim 1 wherein the non-siliconized fragrance solubilizer is selected from the group consisting of PPG-3 myristyl ether, hydrogenated polyisobutene, and C12–15 alkyl benzoate.

16. The composition of claim 1 additionally comprising 0.1–1.0 weight % of a silicone emollient having a refractive index <1.4200 at 21 desirees C. and selected from the groun consisting of:
i) volatile linear polydialkylsiloxanes with a flash point is <100 degrees C.; (ii) nonvolatile linear polydialkylsiloxanes with a flash point is >100 degrees C.; and (iii) silanols in which one or two of the alkyl groups of the foregoing materials (i) or (ii) is replaced with a hydroxyl group.

17. The composition of claim 1 comprising 0.5–2 weight % of the fragrance solubilizer.

18. The composition of claim 1 additionally comprising a fragrance or odor masking component.

19. The composition of any one of claims 1–18 which is free of waxes, cellulosics and alginates.

20. The composition of claim 1 comprising:
(a) 17–23 weight % of an oil phase comprising:
  (i) 10–20 weight % of one or more of the cyclomethicones;
  (ii) 0.6–0.8 weight % of the silicone surfactant; and
  (iii) 0.5–2 weight % of the fragrance solubilizer; and
(b) 77–83 weight % of an aqueous phase comprising:
  (i) 17–25 weight % on an anhydrous basis of the antiperspirant active salt;
  (ii) 4–8% weight % of the water soluble glycol system which comprises at least 0.2% propylene glycol and an additional glycol component selected from the group consisting of dipropylene glycol, tripropylene glycol, 2-methyl 1,3 propanediol, 1,3 propanediol, methyl propylene glycol, low molecular weight polyethylene glycol; and
  (iii) 0.8–3 weight % of the monovalent or divalent ionizable, water soluble inorganic or organic salt.

21. The composition of claim 1 comprising 3–7 weight % of propylene glycol in combination with either 2-methyl propane diol or dipropylene glycol.

22. The composition of claim 1 or claim 20 additionally comprising 1–4 weight % of ethanol or propanol.

23. The composition of claim 1 comprising 9–20 weight % of the cyclomethicones.

24. The composition of claim 1 comprising 0.6–0.8 weight % of the silicone surfactant.

25. The composition of claim 1 comprising 45–65 weight % water.

26. The composition of any one of claims 1–18, 20–24, or 25 which is free of volatile linear silicones and/or free of non-volatile silicones.

* * * * *